US010022108B2

(12) United States Patent
Ohler et al.

(10) Patent No.: US 10,022,108 B2
(45) Date of Patent: Jul. 17, 2018

(54) BOWEL CARE COLLECTION BAG

(71) Applicants: Elizabeth P. Ohler, Seffner, FL (US); Mark K. Ohler, Seffner, FL (US)

(72) Inventors: Elizabeth P. Ohler, Seffner, FL (US); Mark K. Ohler, Seffner, FL (US)

( * ) Notice: Subject to any disclaimer, the term of this patent is extended or adjusted under 35 U.S.C. 154(b) by 324 days.

(21) Appl. No.: 15/007,376

(22) Filed: Jan. 27, 2016

(65) Prior Publication Data

US 2017/0209128 A1 Jul. 27, 2017

(51) Int. Cl.

| | |
|---|---|
| ***A61F 5/44*** | (2006.01) |
| ***A61B 10/00*** | (2006.01) |
| ***A61F 5/441*** | (2006.01) |
| ***A61F 5/443*** | (2006.01) |
| ***A61F 5/451*** | (2006.01) |

(52) U.S. Cl.
CPC .......... *A61B 10/0038* (2013.01); *A61F 5/441* (2013.01); *A61F 5/443* (2013.01); *A61F 5/451* (2013.01)

(58) Field of Classification Search
CPC .......... A61F 5/441; A61F 5/443; A61F 5/451; A61B 10/0038
USPC ......................................... 604/327, 348, 355
See application file for complete search history.

(56) References Cited

U.S. PATENT DOCUMENTS 3,421,506 A * 1/1969 Priebe ...................... A61F 5/44 4/144.3
3,577,989 A * 5/1971 Anderson ............ A61F 5/4401 604/348
3,588,921 A * 6/1971 Nagel ................ A61B 10/0038 4/144.2
3,746,240 A * 7/1973 Flynn ...................... B65D 5/10 206/459.1
4,328,895 A * 5/1982 Jaeger ................ A24F 19/0028 131/231
4,445,898 A * 5/1984 Jensen .................... A61F 5/441 604/332
4,553,969 A * 11/1985 Taylor .................... A61F 5/441 604/355
4,784,656 A * 11/1988 Christian ............. A61F 5/4408 604/332

(Continued)

*Primary Examiner* — Susan Su
(74) *Attorney, Agent, or Firm* — Larson & Larson, P.A.; Frank Liebenow; Justin P. Miller

(57) ABSTRACT

Disclosed is a human waste collection device capable of collecting the human waste products into a collection bag for bedridden and incontinent patients, comprising the first female component, comprising a rectangular shaped base, with triangular sides, front and rear sides and hexagonal top, to adhere with the hexagonal shaped second male component, which thereby adhere together to a single united structure. the female component comprises the slit for receiving the guided barrel of the second male component and the adherent material for attachment with the said second male component at hexagonal top; the circular viewing window, built-in occult for blood testing strip and atleast one of the plurality of gas release holes to release the toxic gases at the first front side. The male component comprises the adhesive liner at the top and bottom sides to adhere with the human anus and first female component respectively. A human waste collection device is sealable, bio-degradable, portable, simple and convenient to use; and adheres to the human skin while in use, providing a sanitized and hygienic environment.

9 Claims, 1 Drawing Sheet

(56) References Cited

U.S. PATENT DOCUMENTS

| | | | | | |
|---|---|---|---|---|---|
| 4,804,377 | A * | 2/1989 | Hanifl | A61F 5/44 | 4/144.2 |
| 4,986,822 | A * | 1/1991 | Anderson | A61F 5/451 | 604/276 |
| 4,990,145 | A * | 2/1991 | Fleury | A61G 9/006 | 604/317 |
| 5,065,459 | A * | 11/1991 | Tjahaja | A61F 5/44 | 4/144.2 |
| 5,368,583 | A * | 11/1994 | Fleury | A61B 5/20 | 600/573 |
| 5,421,827 | A * | 6/1995 | Temple | A61F 5/451 | 383/67 |
| 5,569,225 | A * | 10/1996 | Fleury | A61B 10/0064 | 600/580 |
| 5,593,397 | A * | 1/1997 | La Gro | A61F 5/443 | 604/332 |
| 5,741,239 | A * | 4/1998 | Mulholland | A61F 5/451 | 604/328 |
| 6,116,780 | A * | 9/2000 | Young | A47K 11/02 | 383/44 |
| 7,722,583 | B2 | 5/2010 | Kim et al. | | |
| 7,947,024 | B2 * | 5/2011 | Ramage | A61J 19/00 | 604/317 |
| 8,104,960 | B2 * | 1/2012 | Gill | B65F 1/0006 | 383/36 |
| 8,663,181 | B2 * | 3/2014 | Yang | A61F 5/4408 | 4/144.1 |
| 2001/0034904 | A1 * | 11/2001 | Phillips | A47K 11/06 | 4/484 |
| 2004/0122384 | A1 * | 6/2004 | Evangelista | A61F 5/443 | 604/346 |
| 2005/0010180 | A1 | 1/2005 | Wang et al. | | |
| 2007/0074992 | A1 * | 4/2007 | Fukuda | A61B 10/0038 | 206/528 |
| 2007/0255239 | A1 * | 11/2007 | Hataya | A61F 5/451 | 604/319 |
| 2010/0021089 | A1 * | 1/2010 | Arvizu | B65D 47/243 | 383/42 |
| 2014/0276501 | A1 * | 9/2014 | Cisko | A61F 5/449 | 604/344 |
| 2014/0323909 | A1 * | 10/2014 | Kim | A61F 5/451 | 600/562 |
| 2016/0106570 | A1 * | 4/2016 | Paley | A61F 5/451 | 604/355 |
| 2017/0182196 | A1 * | 6/2017 | Patel | A61L 2/26 | |
| 2018/0049909 | A1 * | 2/2018 | Johnson | A61F 5/4404 | |

* cited by examiner 100
11
10

117
119
117
11
100
10
TIME START:

117
116
117
100
11
110
111
112
10
105
10A
108
106
102
107
TIME START:
103
101
104
10b

BOWEL CARE COLLECTION BAG

CROSS REFERENCE TO RELATED APPLICATION

Not Applicable

FEDERALLY SPONSORED RESEARCH AND DEVELOPMENT

Not Applicable

MICROFICHE APPENDIX

Not Applicable

BACKGROUND OF THE INVENTION

(1) Field of Invention

The present invention relates generally to faecal management devices, particularly to human waste collection devices and, more particularly, to disposable bags for use with such devices, and all being suitable for bedridden and incontinent patients.

(2) Background of Invention

Bedridden and incontinent patients typically require continuous care to dispose of human waste products. Typically, bedridden patients may relieve themselves into a separate receptacle that is then replaced by a caretaker. As the patient has to adjust their position to use the receptacle, such a method of relief may be cause discomfort to the patient for physical reasons as well as for reasons of embarrassment.

Patients unable to move, as well as incontinent patients, are typically incapable of using a separate receptacle for relief. In such cases, human waste products are typically collected on an absorbent pad or similar device that may be fastened to the patient's bed or to the patient themselves. However, such devices are incapable of preventing human waste products from contacting the skin of the patient due to compression of the absorbent pad by the patient's weight. Consequently, the patient may develop pressure ulcers from continued contact with the waste products. Additionally, the necessity of having a caretaker change an unclean absorbent pad may cause further embarrassment for the patient.

Other alternatives for waste collection for bedridden and incontinent patient include waste collection receptacles that may be inserted into a cavity defined in a mattress while the patient is relieving themselves. However this alternative does not prevent the human waste products from contacting the patient's skin due to compression of the mattress and may be difficult to remove while the patient remains on the bed. A similar alternative involves adding a mattress overlay device to address the problem of mattress compression; however for reasons of patient comfort and other factors the device needs to be installed when the patient is ready to relieve themselves and removed immediately following relief, making such a device unsuitable for incontinent patients. Another alternative involves inflating a mattress and inserting a waste collection receptacle into a cavity defined in the mattress when the mattress is inflated; however, this device must similarly be inserted when the patient is ready for relief and removed immediately thereafter, thereby making continuous collection of human waste products impossible.

As such, it may be appreciated that there continues to be a need for a new and improved human waste collection device as set forth by the instant invention which addresses the problems of ease of use as well as effectiveness in construction in providing the ease to collect the human waste into a collection bag for bedridden and incontinent patients, and in this respect, the present invention substantially fulfills this need.

BRIEF SUMMARY OF THE INVENTION

In view of the foregoing disadvantages inherent in the known types of faecal management devices now present in the prior art, the present invention provides a human waste collection device wherein the same provides a bowel care collection bag to collect human waste for bedridden and incontinent patients and use on process of various components employed in the procedure. As such, the general purpose of the present invention, which will be described subsequently in greater detail, is to provide a new and improved faecal management device which has all the advantages of the prior art and none of the disadvantages.

Accordingly, it is a primary aspect of the present invention to provide a human waste collection device utilized for collecting faeces from people unable to control their bowel movement, such as bedridden and incontinent patients. For the purpose, the bowel care collection bag is provided.

In another aspect, the present invention provides a faeces containment device that adheres to the human skin while in use, providing a sanitized and hygienic environment.

It is yet another aspect of the present inventive device comprises a rectangular female component and a hexagonal male component.

Additionally, the present inventive product involves a guided barrel, viewing window, gas release holes and occult blood testing strip.

Further aspect of the present invention provides a hygienic, sealable, bio-degradable, portable, simple and convenient to use human waste collection device.

It is still another aspect of the present invention to provide a new and improved human waste collection device which may be easily and efficiently manufactured and marketed.

It is a further aspect of the present invention to provide a new and improved human waste collection device which is of a durable and reliable construction.

An even further aspect of the present invention is to provide a new and improved human waste collection device which is susceptible to a low cost of manufacture with regard to both materials and labor, and which accordingly is then susceptible of low prices of sale to the consuming public, thereby making such devices economically available to the buying public.

Other aspects of the present invention will become apparent from time to time throughout the specification as hereinafter related.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty which characterize the invention, are pointed out with particularity in the disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

To further clarify various aspects of some example embodiments of the present invention, a more particular description of the invention will be rendered by reference to specific embodiments thereof which are illustrated in the appended drawing. It is appreciated that the drawing depicts only illustrated embodiments of the invention and are therefore not to be considered limiting of its scope. The invention will be described and explained with additional specificity and detail through the use of the accompanying drawing in which.

DETAIL DESCRIPTION OF THE INVENTION

Figures 1, 2, 3:
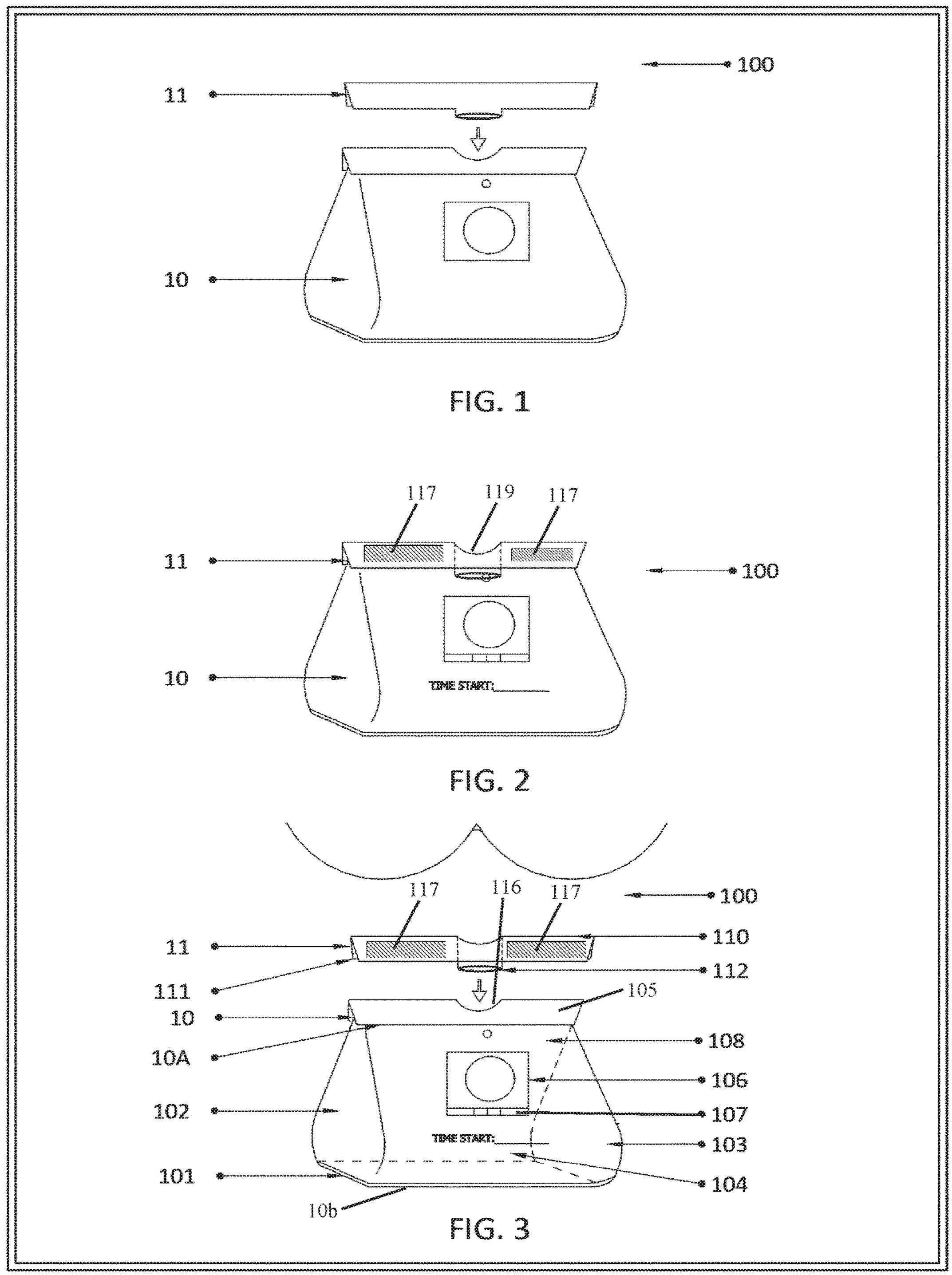
FIG. 1 is a perspective view of the human waste collection device.
FIG. 2 is a graphical representation of the human waste collection device.
FIG. 3 is a perspective view of the human waste collection device.

Various aspects of the illustrative embodiments will be described using the terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

In some preferred embodiments, a human waste collection device utilized for collecting faeces from people unable to control their bowel movement, such as bedridden and incontinent patients is disclosed. The device allows for continuous collection of human waste products while maintaining the bedridden and incontinent patient in a comfortable position.

In one embodiment, the present inventive human waste collection device helps to prevent the occurrence of breakdowns resulting from the skin's frequent contact with fecal matters. In one embodiment, the continuous use of present inventive device eliminates the need of topical ointments, cleansing solutions, disposable and washable bed pads, antibiotic creams or medicaments to eradicate the infection, skin protectants, disposable wipes and other related bowel care toiletries. In one embodiment, the present inventive device facilitates preventing human waste products from contacting the skin of the patient, thereby substantially reducing the occurrence of pressure ulcers. In one embodiment, the present device for collection of human waste products allow for an easy and efficient process of waste product disposal, thereby reducing the physical and emotional discomfort of the patient, and with careful containment of human waste into a well-designed bag, the contamination is diminished, and thus preventing the patient and caregiver from contracting the ailments.

With reference now to the drawings, and in particular to FIGS. 1 to 3 thereof, a new and improved human waste collection device embodying the principles and concepts of the present invention are described herein.

Referring to FIG. 1 and FIG. 2, an embodiment of the human waste collection device according to this invention is designated generally by the reference character 100. The overall assembly of the waste collection device includes generally rectangular first part, female component 10 and hexagonal second part, male component 11.

As shown in FIG. 3, the preferred embodiment of the present invention discloses the first female component 10, which is 8 inches wide and 10 inches long, designed similar to a conventional "brown bag" like structure comprising a rectangular shaped base 101, with triangular sides 102, front and rear sides 103, 104 and hexagonal top 105. The hexagonal top 105 comprises the slit 116 for receiving the guided barrel 112 of the second male component 11. The hexagonal top 105 comprises the adherent material for attachment with the second male component 11.

Another embodiment discloses the first female component 10 comprising a circular viewing window 106 at the first front side 103 that allows the caregiver a clear view of the amount of fecal matter being deposited inside the bag. Also, at the first front side 103, the first female component 10 comprises a built-in occult blood testing strip 107, utilized for on-spot testing of the presence of blood in the stool.

In further embodiment, the first female component 10 also comprises at least one gas release hole 108 which permits the bag to be periodically opened to permit gases accumulated therein to be expelled, or fecal matter to be removed and the bag to remain on the patient.

In accordance with the disclosed embodiments, the first female component 10 comprises the two separate compartments itself. The first compartment 10*a* conjoined with the male component 11 and used to house the liner or the flat adherent part of the contraption after use. The second compartment 10*b* involves the plastic bag that can be easily pulled out from a pocket at the bottom. This plastic bag will prevent splatters and leakage and will effectively keep the waste products contained therein, prior to proper disposal.

Furthermore referring to FIG. 3, another embodiment discloses the prospects of the second male component 11, comprising the liner material at its top side 110 that adheres to the buttock area covering the human anus, and the bottom side 111 also comprising the adherent material for attachment with the first female component 10. The second male component 11 is hexagonal in design and shape with a guided barrel 112, which helps to retain the faecal waste products and prevents the messing of waste products.

A specifically shaped adhesive applicator is provided to enable a nurse or physician to easily adhere the human waste collection device 100 and to conveniently and securely attach the adhesive 117 located about an upper opening 119 of the male component to the skin about the anus, and thereby providing a hygienic bowel care.

As may now be appreciated from the above description and reference to the accompanying drawings, the present invention provides a human waste collection device which may be utilized by the nurses or caregivers to ease the collection of the human waste into a collection bag for bedridden and incontinent patients.

It is to be understood that the above description is intended to be illustrative, and not restrictive. For example, the above-discussed embodiments may be used in combination with each other. Many other embodiments will be apparent to those of skill in the art upon reviewing the above description.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A human waste collection device capable of collecting human waste products from a patient, comprising:

a) a female component, comprising a rectangular shaped base, with triangular sides, front and rear sides and a hexagonal top; and b) a male component, hexagonal in shape, comprising an upper opening and a guided barrel to meet with the female component:

wherein the said hexagonal top comprises a slit for receiving the guided barrel of the male component and an adherent material for attachment with the male component;

wherein the male component comprises an adhesive liner on a top side about the upper opening for adhering to skin about the patient's anus;

wherein the female component and the male component adhere together to form a single united structure.

2. The human waste collection device of claim 1, wherein the front side of the female component further comprises a circular viewing window to allow the caregiver a clear view of the amount of fecal matter being deposited inside the female component.

3. The human waste collection device of claim 1, further comprising an occult blood testing strip, utilized for on-spot testing for the presence of blood in the stool.

4. The human waste collection device of claim 1, wherein the female component of the human waste collection device comprises gas release holes which permits the human waste collection device to be periodically opened to permit gases accumulated therein to be expelled, or fecal matter to be removed while the human waste collection device remains on the patient.

5. The human waste collection device of claim 1, wherein the male component of the said human waste collection device comprises the guided barrel to retain the fecal waste products and prevents the messing of waste products.

6. The human waste collection device of claim 1, wherein an adherent material is on a bottom side of the male component of the human waste collection device for attachment with the female component.

7. The human waste collection device of claim 1, wherein the human waste collection device is configured to adhere to the patient while in use, providing a sanitized and hygienic environment.

8. The human waste collection device of claim 1, wherein the human waste collection device enables a nurse or physician to adhere the human waste collection device to the skin about the patient's anus and to securely attach the adhesive liner to the skin about the patient's anus, and thereby providing a hygienic bowel care.

9. The human waste collection device of claim 1, wherein the human waste collection device is sealable, bio-degradable, and portable.

* * * * *